Dec. 31, 1968 H. C. SWIM ET AL Plant Pat. 2,853
ROSE PLANT
Filed May 11, 1967
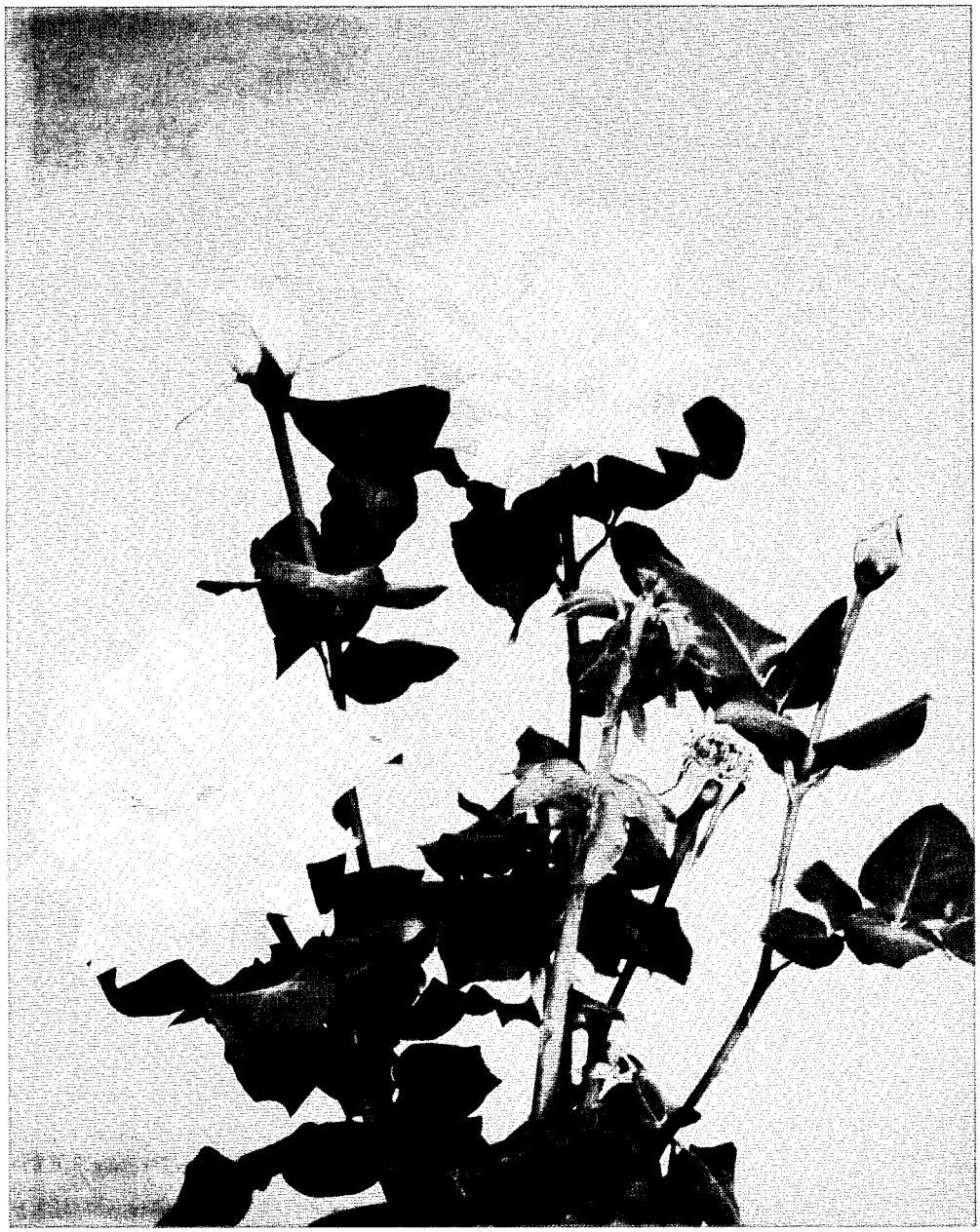
Inventors.
H. C. Swim
O. L. Weeks
By: Robb & Robb
Attorneys.

United States Patent Office

Plant Pat. 2,853
Patented Dec. 31, 1968

2,853
ROSE PLANT

Herbert C. Swim, Ontario, and O. L. Weeks, Chino, Calif., assignors, by mesne assignments to O. L. Weeks, doing business as Weeks Wholesale Rose Grower, Chino, Calif.

Filed May 11, 1967, Ser. No. 637,853
1 Claim. (Cl. Plt.—14)

The present invention relates to a new and distinct variety of rose plant of the hybrid tea class, which was originated by us by crossing the variety known as "Mount Shasta" (Plant Patent No. 2,132) with the variety known as "White Knight" (Plant Patent No. 1,359), the former being the seed parent and the latter being the pollen parent.

As the result of this breeding, we have produced a new and improved rose variety which is distinguished from its parents, as well as from all other varities of which we are aware, as evidenced by the following unique combination of characteristics which are outstanding therein:

(1) A vigorous and bushy plant habit, with the plants having good resistance to powdery mildew as compared with other varieties grown under comparable conditions;

(2) Large, dark green leaves having a distinctive silvery cast;

(3) Heavily pigmented new growth;

(4) Strong, stiff and erect stems on which the flowers are always borne in an upright position;

(5) A habit of bearing a large majority of the flowers singly to the stems;

(6) An urn-shaped flower bud form which opens to large, high-centered white or nearly white flowers of good petalage; and (7) A substantial flower petal substance as compared with most other white roses of the hybrid tea or grandiflora classes, with consequent resistance to blemish by rain, heat and other adverse weather conditions.

In comparison with its seed parent "Mount Shasta," the new variety is typically shorter in growth and substantially more thickly branched or bushy; the new variety produces its flowers more generally singly to the stems, with only occasional stems having two or more flowers, contrary to this parent variety; it has substantially greater flower petalage; and a substantial number of its ovaries are borne on the top of the receptacle or hypanthium so that they are exposed, contrary to the parent variety.

As compared with its pollen parent, "White Knight," the new variety exhibits substantially greater vigor as measured by the length of the stems when grown in Southern California; its foliage is dark green with a silvery cast, contrary to the light green foliage with a yellow cast of this parent; the foliage has substantially greater resistance to powdery mildew than this parent; and the new variety has noticeably more yellow pigment in the central portion of the opening or newly opened flowers than in the flowers of this parent.

Asexual reproduction of our new variety by budding, as performed at Chino, Calf., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Nickerson Color Fan, published by Munsell Color Company, Inc., of Baltimore, Md., except where general color terms of ordinary dictionary significance are obvious:

Type: Medium height; bush, outdoor; seedling; for cut flowers and for garden decoration.

Class: Hybrid tea.

Breeding: Seedling.

*Seed parent.*—"Mount Shasta."

*Pollen parent.*—"White Knight."

Propagation: Holds its distinguishing characteristics through succeeding propagations by budding.

*Flower*

Locality where grown and observed: In a greenhouse at Chino, Calif.

Flowers borne: Generally singly, but sometimes two or three to stem; on strong stems of medium length.

Quantity of bloom: Moderately free, both outdoors and in greenhouse.

Continuity: More or less continuous.

Fragrance: Slight.

*Nature.*—Tea.

Bud:

*Peduncle.*—Long; medium-heavy caliper; erect; smooth, except for many delicate, fragile, more or less straight hairs. Color—Yellowish-Green.

*Before calyx breaks.*—Size—medium. Form—short; pointed; with a conspicuous neck; without foliaceous appendages on the surface of the bud; sometimes with stout, entire foliaceous parts extending beyond the tip of the bud equal to ½ of its length.

*As calyx breaks.*—Color—Brilliant Yellow Green, Plate 2.5GY9/8.

*As first petal opens.*—Size: Medium-large. Form: Long; urn-shaped. Color: Outside—white, except for small area at base from near Brilliant Yellow Green, Plate 7.5GY8/7 to Brilliant Yellow Green, Plate 5GY8/8, with this greenish color following veins briefly. Inside—white, except for small basal area of Brilliant Yellow Green, Plate 5GY8/8.

*Opening.*—Opens up well.

Bloom:

*Size (when fully open).*—Large; from 4½ inches to 4¾ inches.

*Petalage.*—Double, but stamens not hidden; from 30 to 36 petals plus 4 to 6 petaloids arranged regularly, except in center where petals become somewhat irregular in shape.

*Form.*—High-centered at first, but becoming cupped to globular in center; petals being at first loosely rolled outward but becoming later more tightly rolled outward emphasizing the apical point, but with center of flower usually finishing cup-like at maturity.

Petals:

*Texture.*—Thick; leathery.

*Appearance.*—Inside—crepey. Outside—satiny.

*Shape.*—Outside—nearly round but broader than long, with apex having 1 notch or entire. Intermediate—broadly obovate, with apex shallowly acute; scalloped slightly near base. Inside—obovate; scalloped irregularly with apex usually having 1 notch; often wrinkled and irregular in shape.

This description of a newly opened flower was made from a rose grown in a greenhouse during the month of March at Chino, Calif.:

*Color.*—Outer petal: Outside surface—white, except for small basal area near Brilliant Yellow Green, Plate 5GY8/8, with some extension of this color on veins. Inside surface—white, except for small basal area near Brilliant Yellow Green, Plate 2.5GY9/8, with this color extended briefly on veins. Intermediate petal: Outside surface—white or nearly so, except for small area at base near Brilliant Yellow Green, Plate 5GY8/8, extended briefly on veins. Inside surface—white or nearly so, except for small basal area of Brilliant Greenish-Yellow, Plate 2.5GY9/8, extended briefly on veins. Inner petal: Outside surface—white, except for very small basal area of faint green extending briefly on veins. Inside surface—white or nearly so, except for small area at base near Brilliant Greenish-Yellow, Plate 2.5GY 9/8, extending upward on veins about ⅓ their length.

This description was made from a rose that was open for three days indoors during the month of March at Chino, Calif.:

*Color.*—Outer petal: Outside surface—white, except for faint greenish color in small area at base. Inside surface—white, except for small area at base which is faintly green. Inner petal: Outside surface—white, except for small area at base which is faintly yellow. Inside surface—white, except for small basal area that is faintly yellow.

*General color effect.*—Newly opened flower—white, except for central area which is a creamy yellow color, 3-days open—white, except for markings on petaloids in central part which are pink to red.

*Behavior.*—Drop off cleanly; occasional petaloids persist.

*Flower longevity.*—Cut roses grown in greenhouse and kept at living room temperatures—5 days in March.

*Reproductive organs*

Stamens: Medium quantity; arranged fairly regularly about pistils and mixed wth petaloids.

Filaments: Long, most with anthers.

*Color.*—From reddish to pink.

Anthers: Small for class; all open at various times.

*Color.*—Yellow.

Pollen: Moderate quantity.

*Color*—Gold.

Pistils: Medium quantity.

Styles: Uneven; short; from thin to medium caliper; loosely bunched.

Stigma:

*Color.*—Buff.

Ovaries: Some enclosed in, but many protruding from calyx.

Hips: Short; globular in general outline; very smooth; walls thick and fleshy.

*Color.*—Yellow at maturity.

Sepals: Permanent; moderate length; spear-shaped; recurved.

Seeds: From few to many; from small to medium in size.

*Plant*

Foliage:

*Leaves.*—Compound of 3–5 leaflets; from sparse to normal quantity; from medium to large size; heavy; leathery.

*Leaflets.*—Terminals broadly ovoid and laterals ovoid. Apex—acute. Base—round. Margin—simply serrate.

*Color.*—Mature: Upper surface—Dark Green. Under surface—Grey-Green. Young: Upper surface—Yellow Green, with Red margins and veins and some overlay of Red. Under surface—veins are light Green and remainder bright Reddish-Purple.

*Rachis* (*the supporting stem of the compound leaf*).—Medium weight. Upper side—grooved; lined with short stipitate glands. Under side—sparsely prickly; few stipitate glands and small quantity of fine short hairs.

*Stipules.*—Moderately short; moderately wide; with short points turning out at an angle of more than 45°.

*Disease resistance.*—Substantially resistant to powdery mildew when compared with other varieties of white hybrid tea roses grown under glass under comparable conditions at Chino, Calif.

Growth:

*Habit.*—Moderately tall; bushy; much-branched.

*Growth.*—Vigorous.

*Canes.*—From medium to heavy caliper.

*Main stems.*—Dull Color: Dark Yellow-Green. Large prickles: Several; short; straight; with short broad base; color—Light Brown. Small prickles—few; color—Light Brown. Hairs: None.

*Branches.*—Color: Dull Medium Yellow-Green. Large prickles: Several; short; straight; with short broad base; color—from Dark Brown to Light Yellow-Green, depending on age. Small prickles: Few; color—Brown. Hairs: None.

*New shoots.*—Color: Light Yellow-Green with some Red overlay. Large prickles: Several; from short to medium length; straight to slightly hooked downward; with short narrow base. Color—Light Red, with light Green tip. Small prickles: Few. Color—Reddish, with Green tips. Hairs: None.

We claim:

1. A new and distinct variety of rose plant of the hybrid tea class, substantially as herein shown and described, characterized particularly as to novelty by the unique combination of a vigorous and bushy plant habit, with the plants having good resistance to powdery mildew as compared with other varieties grown under comparable conditions, large, dark green leaves having a distinctive silvery cast, heavily pigmented new growth, strong, stiff and erect stems on which the flowers are always borne in an upright position, a habit of bearing a large majority of the flowers singly to the stems, an urn-shaped flower bud form which opens to alrge, high-centered white or nearly white flowers of good petalage and a substantial flower petal substance as compared with most other white roses of the hybrid tea or grandiflora classes, with consequent resistance to blemish by rain, heat and other adverse weather conditions.

No references cited.

ROBERT E. BAGWILL, *Primary Examiner.*